United States Patent [19]
Waggener et al.

[11] Patent Number: 5,227,969
[45] Date of Patent: Jul. 13, 1993

[54] MANIPULABLE THREE-DIMENSIONAL PROJECTION IMAGING METHOD

[75] Inventors: Robert G. Waggener, Lytle; Jory Lange, San Antonio, both of Tex.

[73] Assignee: W. L. Systems, Inc., San Antonio, Tex.

[21] Appl. No.: 707,204

[22] Filed: May 23, 1991

Related U.S. Application Data

[63] Continuation of Ser. No. 226,840, Aug. 1, 1988, abandoned.

[51] Int. Cl.$^5$ .................... G06F 15/42; A61N 5/00
[52] U.S. Cl. ...................... 364/413.26; 364/413.13
[58] Field of Search ................ 364/413.01, 413.13, 364/413.26, 413.22; 340/724, 727, 729; 358/183; 382/6; 395/137, 138, 139

[56] References Cited

U.S. PATENT DOCUMENTS

| | | | |
|---|---|---|---|
| 3,060,924 | 10/1962 | Rush | 128/1.2 |
| 3,871,579 | 3/1975 | Inamura | 364/413.26 |
| 3,987,281 | 10/1976 | Hodes | 364/413.26 |
| 4,398,189 | 8/1983 | Pasierb, Jr. et al. | 340/727 |
| 4,455,609 | 6/1984 | Inamura et al. | 364/414 |
| 4,630,203 | 12/1986 | Szirtes | 364/413.26 |
| 4,710,876 | 12/1987 | Cline et al. | 364/413.22 |
| 4,729,099 | 3/1988 | Iverson et al. | 364/413.26 |
| 4,827,344 | 5/1989 | Astle et al. | 358/153 |
| 4,862,272 | 8/1989 | Karlock | 358/151 |

FOREIGN PATENT DOCUMENTS 2600328  7/1977  Fed. Rep. of Germany.

OTHER PUBLICATIONS

Matsuo et al., "A three dimensional . . . ", Conference: MEDINFO 80 Proceedings of the Third World Conference of Medical Inforatics, Sep. 29–Oct. 4, 1980, Tokyo, Japan pp. 18–23.
Abadir et al., "A feasibility study of computerized tomography radiation therapy treatment planning in transverse, coronal and saggital sections", *Int. J. Radiat. Oncol. Biol. Phys.* (U.S.A.), No. 4, 1978, pp. 11–12 (abstract only).
Irifune et al., "Development of a CT based 3-D radiation treatment planning system", Conf: Proceedings of the 8th International Conference on the Use of Computers in Radiation Therapy, (Cat. No. 84CH2048-7) IEEE Comput. Soc. Press, Jul. 9–12, 1984, pp. 205–209 (abstract only).
Brewster et al., "Dose Distribution Display Techniques in Radiation Therapy", Conf: NCGA 8th Conference, Philadelphia, Pa., Mar. 22–26, 1987, p. 45 (abstract only).
Mohan, et al., "Arbitrary oblique image sections for 3-D radiation treatment planning", *Int. J. Radiat. Oncol. Biol. Phys.* (U.S.A.), 13(8), Aug. 1987, pp. 1247–1254 (abstract only).
Yoichiro Umegaki, "Development of Computer Systems for Radiotherapy of Cancer" Japanese Journal of Clinical Oncology, vol. 1, No. 1, Jan. 1971.
Theodor D. Sterling, et al., "Dynamic Display of Radiotherapy Plans Using Computer-Produced Films", (List continued on next page.)

*Primary Examiner*—Roy N. Envall, Jr.
*Assistant Examiner*—D. Huntley
*Attorney, Agent, or Firm*—Vaden, Eickenroht, Thompson, Boulware & Feather

[57] ABSTRACT

A method of developing a foreground image from two views of an object, such as orthogonal x-ray views, for the making of a projectable three-dimension image on a computer display monitor superimposed on a background image. The foreground image can be included on the original view of the object or can be separate therefrom or can be represented by digital mathematical expression. The method finds particular application in medical applications such as brachytherapy dosimetry, breast biopsy localizing, and external dosimetry computation for radiotherapy. When used with a dosimetry application, isodose lines can be computed and imaged for various simulated positioning and orientation of the radiation sources and simulated dose sizes.

21 Claims, 4 Drawing Sheets

OTHER PUBLICATIONS

Work In Progress, vol. 107, Radiology Jun., 1973 H. Dahlin, Elteknic (Sweden) vol. 20, No. 5, Mar. 1977.
Gabriel K. Y. Lam, et al., "Automated Dose Mapping System for the TRIUMF Biomedical Pion Beam", Phys. Med. Biol., vol. 23, No. 4, Jul. 1978.
R. G. Dale, "Implementation of the Philips Treatment Planning System for Use in Radiation Therapy", vol. 51, No. 608, Aug. 1978.
L. Dutori, et al., "A Brachytherapy Program Used with the Philips Treatment Planning System", Medicomundi (Netherlands) vol. 24, No. 3, 1979.
Nucletron, Microselectron LDR.MDR, 1-21.

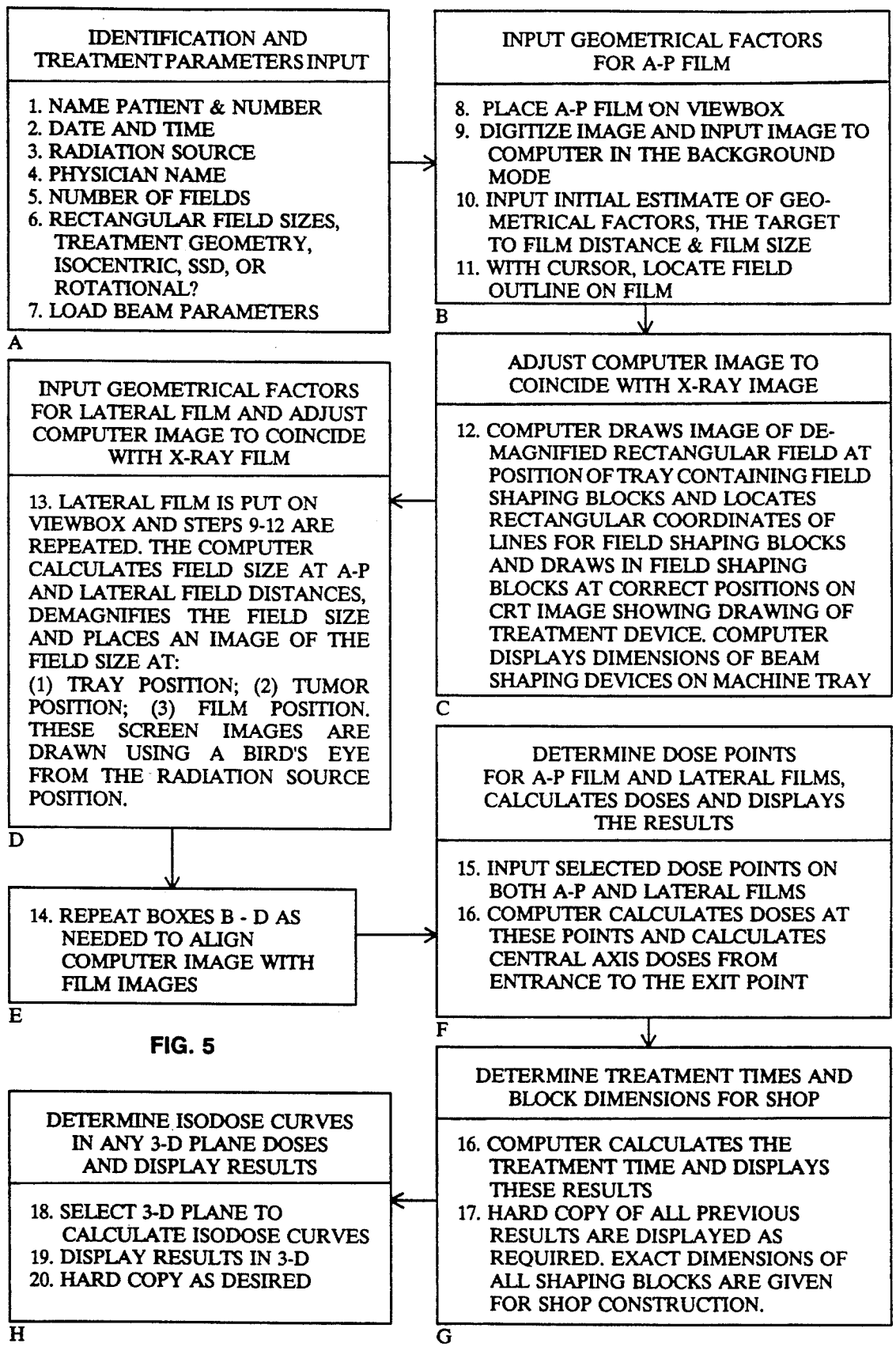

MANIPULABLE THREE-DIMENSIONAL PROJECTION IMAGING METHOD

This application is a continuation of co-pending application Ser. No. 07/226,840, filed on Aug. 1, 1988, now abandoned.

BACKGROUND OF THE INVENTION

1. Field of the Invention

This invention pertains to the computerizing of images for manipulation purposes and more specifically to the creation of data computed three-dimensional images for image projection and manipulation.

2. Description of the Prior Art

Images of objects can be created in numerous ways including photographs, negatives of photographs, x-ray radiographs, computed tomography images, magnetic resonance images, ultrasound images, and nuclear medicine scan images. All of these images produce a planar representation of the imaged object. When the imaged object is to be viewed relative to another imaged object, it is conventional to do so by having one of the objects, namely, the foreground object, put on a transparency so that the two images can be moved relative to one another. Alternatively, one object can be photographically projected on the other.

In either of the above cases, it is possible to shift one object up or down or sideways or a combination to orient one with other. It is not possible, however, with such planar object images to rotate or turn one object with respect to the other into or out of plane since both images are in two dimensions.

Although a second image view of the objects can be created in the same manner as the first, the second relationship of the object is still a planar relationship. It is still not possible to rotate one of the two images with respect to the other into or out of the plane.

An example of the use of two planar views of the type just described is in brachytherapy or the treatment of malignant tumors using implants of radioactive sources. When the tumor or tumors under treatment are in the vaginal area of the body, a Fletcher Suit Delclos gynecological applicator is commonly employed. Such a device is in the form of two components, a hollow cylinder that accepts a plurality of sequential or tandem radiation sources and a pair of ovoids, each of which accepts one source. In use, the applicator is inserted and positioned in the area of the tumor(s) to be treated. Positioning includes axial and lateral location as well as rotation. Once the device is properly positioned within the patient the radioactive sources are then inserted into the applicator components.

When such a radioactive implant is employed, it is important for the attending physician to know exactly where the sources are located to determine the distribution of the radiation dosage delivered by the implant. The physician is interested not only in the dose that is received by the tumor(s) but also that which is received by the surrounding normal body structures. This information allows the physician to design the implant so that the tumor(s) will receive an adequate therapeutic dose without exceeding the tolerance dose of the surrounding normal structure. In order to obtain the information required to describe the dose distribution characteristics of a particular implant, the exact location and orientation of the radioactive material or sources within the implant must be determined. Typically, two or more x-ray images of the implant are employed for the determination. The procedure involves mapping the location of each individual radioactive source in each of two x-ray film views and then entering this information into a computer. The computer then calculates and describes the dose distribution of the implant in question, all of which can be extremely time consuming. A particular problem occurs in this regard when the x-ray films are sub-optimal.

Therefore, it is a feature of the present invention to create a three-dimensional foreground image projection that can be manipulated in an universal manner, including rotation, with respect to a background image.

It is another feature of the present invention to utilize a three-dimensional foreground image of a device as one or more radiation dose sources and automatically determine the isodose mapping characteristics thereof with respect to a background image.

SUMMARY OF THE INVENTION

The method of creating a manipulable computerized, three-dimensional image projection of an object with respect to an environmental background, in a preferred embodiment, generally utilizes a view box for holding an x-ray or other image of the object, a video camera for recording a video image of the object, a digitizer, a computer with appropriate storage or memory facilities, computer controls and display monitor, and appropriate operational software.

The image on the view box normally includes an environmental background image and a foreground image. A first planar representation of the background and foreground images are recorded and digitized for displaying on the computer monitor and then a second planar representation of the background and foreground images, orthogonal with the first is recorded and digitized. The digitized images of the foreground in the two representations or views are used to create a three-dimensional data geometric representation stored in the computer.

Then, one of the background and foreground planar representations or views is displayed in a background mode on the computer monitor and overlaid with a projection in the same plane of the three-dimensional data geometric representation of an image in the foreground mode. Using the computer controls, the projection of the foreground image is located and manipulated, including possibly rotation, with respect to the background image. The same procedure can be followed with respect to the other planar background representation.

When the invention is employed in a brachytherapy application, the background representation can be represented by the x-ray films of an anterior-posterior view and a lateral view of a patient. The foreground representation is of the source applicator. Once a source applicator is established for a "try" condition, individual source values for the doses in the applicator are assumed and the composite isodose lines are automatically calculated and displayed with respect to the background. From known characteristics of the anatomy, it can be determined if particularly sensitive body parts would be overly exposed under such dosage conditions as well as if sufficient radiation treatment is provided for the tumor(s).

Additional background displays can be provided by other video displays fiducially aligned with the first background display. For example, an MRI display showing soft tissue can be displayed with an x-ray display showing hard structure.

Also, a foreground display can be provided by a separate video camera from that employed for video imaging the background, if desired.

Alternatively to video recording the foreground object, a direct data description thereof can be inputted into the storage system. This procedure is particularly valuable in creating a three-dimensional representation of an external foreground object with respect to the background object, rather than when the foreground object is an implant.

BRIEF DESCRIPTION OF THE DRAWINGS

So that the manner in which the above-recited features, advantages and objects of the invention, as well as others which will become apparent, are attained and can be understood in detail, more particularly description of the invention briefly summarized above may be had by reference to the embodiments thereof that are illustrated in the drawings, which drawings form a part of the specification. It is to be noted, however, that the appended drawings illustrate only preferred embodiments of the invention and are, therefore, not to be considered limiting of its scope for the invention may admit to other equally effective embodiments.

IN THE DRAWINGS

Figure 1:
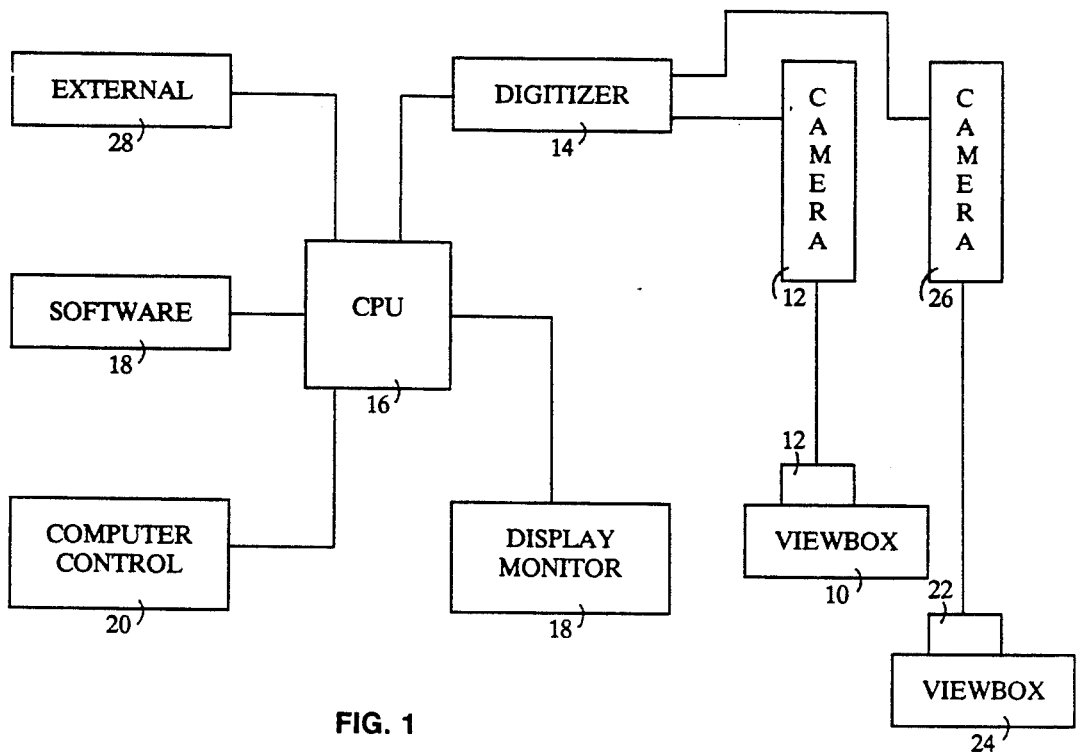

FIG. 1 is a block diagram of a preferred embodiment of the hardware required to implement the invention methods, including additional options.

Figure 2:
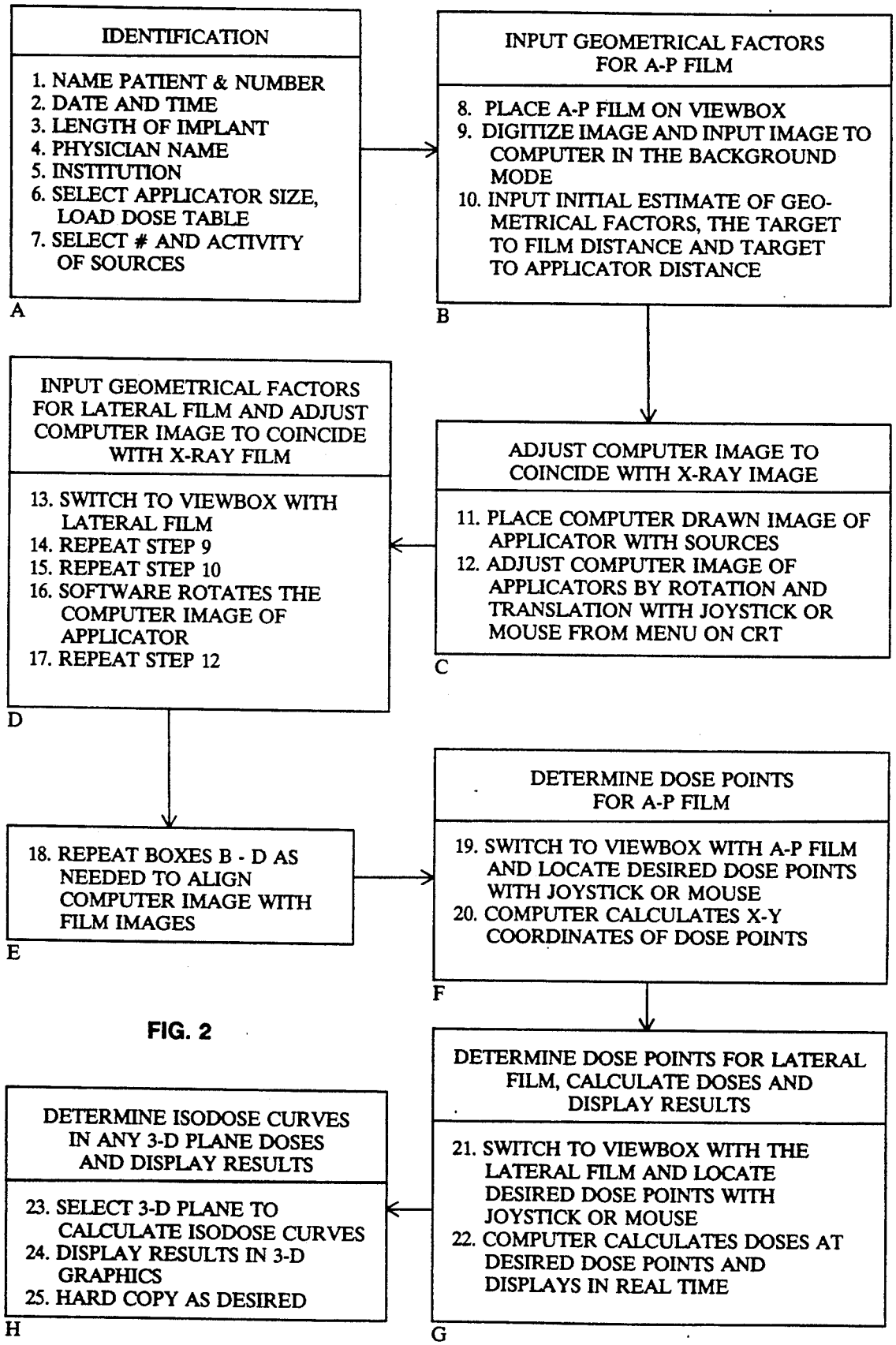

FIG. 2 is a flow diagram of the inventive method implemented in a brachytherapy dosimetry procedure employing the use a radiation source implant in the form of a tandem applicator.

Figure 3:
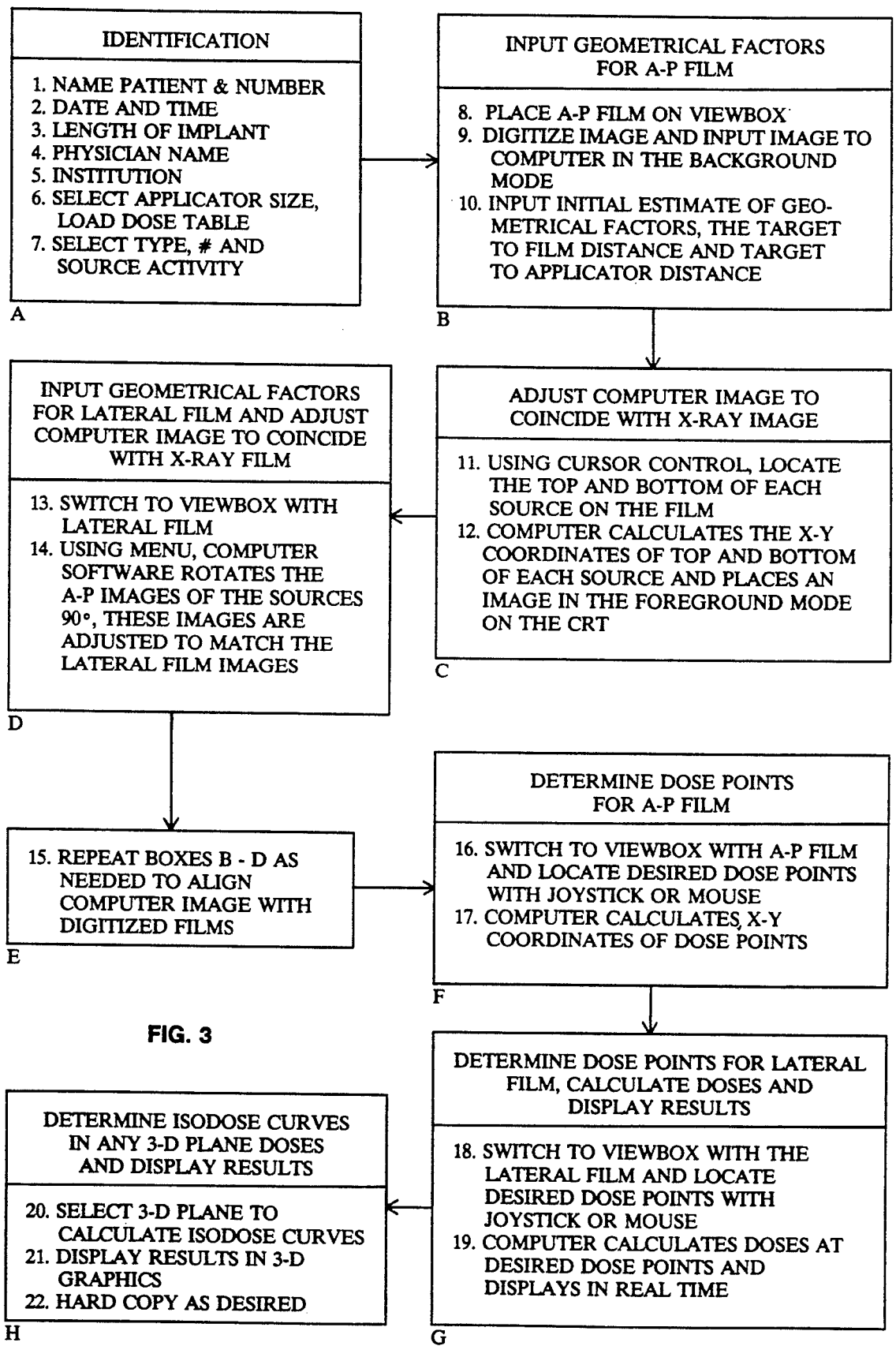

FIG. 3 is a flow diagram of the inventive method implemented in a brachytherapy dosimetry system employing the use of a radiation source implant in the form of a wire or needle.

Figure 4:
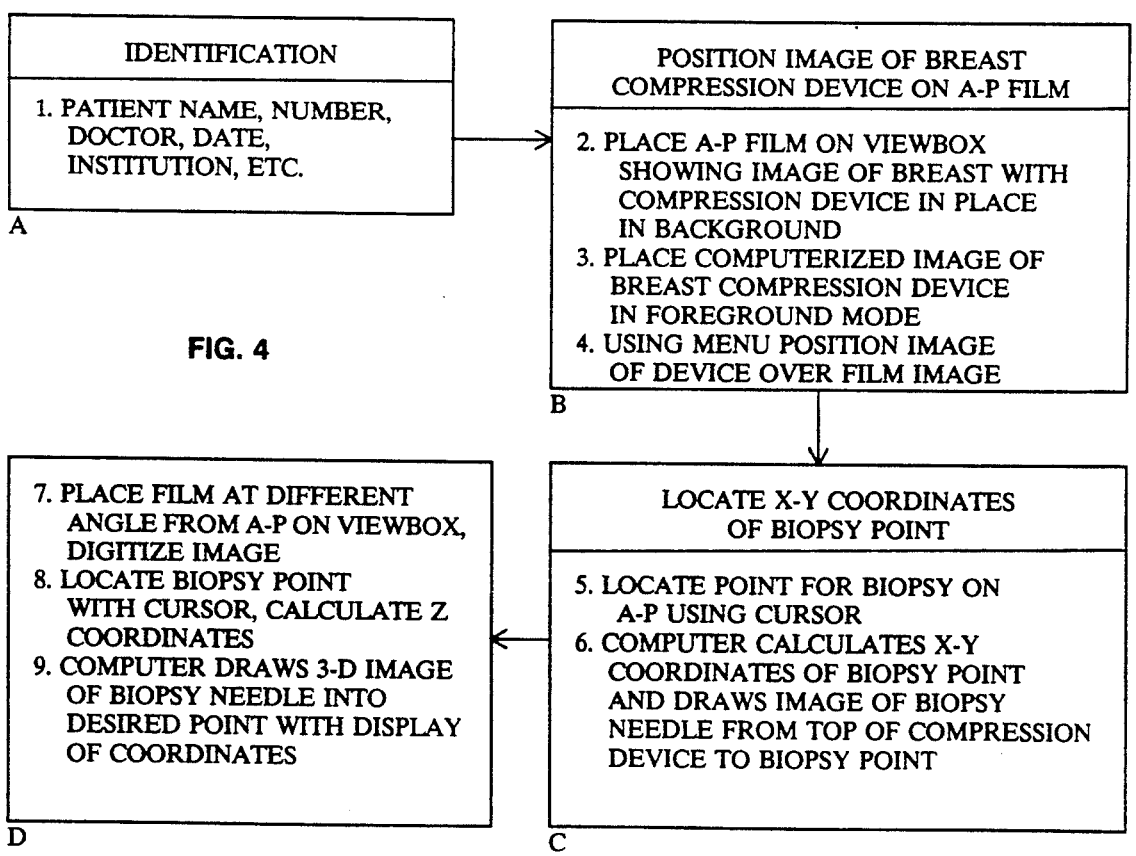

FIG. 4 is a flow diagram of the inventive method implemented in a breast biopsy or surgery procedure.

FIG. 5 is a flow diagram of the inventive method implemented in an external beam radiotherapy procedure.

DESCRIPTION OF THE PREFERRED EMBODIMENTS

The method of the invention generally pertains to creating and locating through orientation and positioning the projection of an object in three-dimensional space using two views of the object, typically captured on film using x-rays or gamma rays to expose the film. Other photographic images or even the object itself viewed at different viewing angles can be employed.

Turning to FIG. 1, a block diagram of a preferred embodiment of the equipment for implementing the method is shown. A lighted view box 10 is employed for receiving an image 12 of the object. Typically, the image is of a background object and the foreground object together, as will later be described by example. A video camera 12 creates a video image of the image located on the view box and passes that image to a digitizer 14, which, in turn, is connected to the memory or CPU portion 16 of the computer system. The CPU is connected to display monitor 18, which is capable of displaying the digitized image stored in the CPU. Software 18 suitable for performing the functions hereafter described is connected to the CPU and computer control 20 is connected to the CPU for inputting the control commands as hereafter described.

The setup just described is suitable when the background object and the foreground object are both included in image 12. When the two objects are not on the same original image view, then one image is placed on view box 10 and the other image 22 is placed on a second view box 24. A video camera 26 focused on image 22 produces a video image of image 22 and transmits that image to digitizer 14.

In some instances, the image to be created in the CPU as hereafter described is already in an external digital format. In such case, an external digital storage means 28 in the form of an appropriate disc, tape or other medium connected to CPU 16 is employed.

Referring to FIG. 2, an example of a brachytherapy procedure is outlined using the equipment shown in FIG. 1. Block A includes the identification information specific to the procedure and is appropriately inputted into the computer to identify the stored data with the appropriate identification. The patient's name and number, the date and time, the length of the applicator implant to be used with the patient, the physician's name, the hospital or other institution, the selected applicator size or other dimensions and the selected number and activity of the individual radiation sources are, for example, inputted into the computer. Now turning to Block B, the anterior-posterior view is placed on view box 10 as image 12 and a digitized image thereof is produced to the computer, all in background mode to begin with. Typically, the film will show the vaginal area of the patient with an implant in a preliminary position.

The operator then estimates all of the geometrical scaling factors scaling pertaining to the target or foreground object, in this case the implant. Now turning to Block C, the operator creates a computer drawing or line image of the foreground object, making appropriate adjustment with a joystick, mouse or the like to make the line image correspond to the background image displayed on the display monitor.

Image 12 is then replaced with a lateral view of the patient, as shown in Block D, which is a view that is orthogonal with the A-P view previously used. The necessary steps are repeated as above to create a line image of the foreground. The software package includes appropriate three-dimensional computer graphics well-known in the art to allow the rotation of the foreground line image and its universal translation with respect to the background image on the display monitor, either the A-P view or the lateral view as selected by the operator. Actually what is being shown in line image representation is a projection of a three-dimensional image of the foreground object. Such a projection is sometimes referred to as a "virtual" image.

The applicator implant is designed to accept a plurality or tandem of individual radiation sources. To determine the overall dose at sensitive points on the background, both the tumor or tumors to be treated as well as the anatomical body points that are easily damaged by excessive radiation, data regarding various size sources are inserted into the individual source positions in the implant and isodose lines are automatically drawn. It is apparent that the implant can be subsequently repositioned and/or the individual doses can be changed to cause new isodose lines to be created until the proper combination of implant position and dosage selection is finalized. Then a hard copy is made, usually of both the A-P view and the lateral view.

Referring to FIG. 3, a second brachytherapy dosimetry system is shown in outline form wherein the radioactive source is a wire or a needle. The procedure is virtually the same as for the previous procedure, except that a wire or needle need not necessarily already be included in the A-P and lateral views of the background. The operator, in this case, merely locates where the top and bottom of the wire or needle source should be and accordingly creates an appropriate line image thereof as before.

The invention procedure is also useful for the three-dimensional localization of a point for stereotactic breast biopsy or surgery. The procedure is outlined in FIG. 4. Generally, a computer drawing is made of a breast compression device as the background object that is used to immobilize the female breast for purposes of locating a site for needle biopsy. Two x-ray films or views are taken of this immobilization device with the breast in place at different angles, generally an A-P view and another at a different angle, which may be different from an orthogonal angle. It should be noted that three-dimensional views can be simulated using appropriate software packages from views that are not orthogonal. The A-P file of the immobilization device and breast is placed on the viewbox, digitized and placed in the background mode on the computer display monitor or CRT. The operator, using a mouse or cursor, locates the site for biopsy on the first film. Thus, the biopsy site is described in two dimensions. The other film taken at a different angle is then placed on the view box and the spot for tumor biopsy is likewise located on this film with the cursor or mouse to locate the biopsy point in a third dimension. The computer program of the software package then calculates the exact coordinates for the biopsy needle represented in the foreground mode to be inserted on the immobilization device and the exact distance for it to be injected.

The previous procedures have assumed that a foreground image is implanted or within the background image. That is not always the case. FIG. 5 outlines a procedure for external dosimetry computation for radiotherapy. In this case, x-ray images of the patient in the treatment position are placed on the view box. Computer generated drawings of the external devices associated with the treatment, for example, blocks, shields, filters and the like, are drawn on the screen in the foreground mode and superimposed over the localization film. The drawn objects, which are in the foreground mode as that term has been used herein, are rotated and translated until the shadow they cast on the computer screen or display monitor is satisfactorily placed. Once the operator is satisfied, the computer initiates the computation of the radiation doses at the different points in the treatment field and displays them using the computer graphics superimposed over the images of the patient.

Although the examples above have referred to medical applications, it is apparent that the procedure has application to non-medical uses, as well. For example, room settings can easily be developed in a foreground mode for placement within a room shown in the background mode. With two background views, not only the overall plan view can be developed, but also a lateral view can be shown.

In certain applications, it is possible to superimpose two different kinds of image representations both in the background mode. For example, an x-ray image of the skeletal structure can be superimposed with an MRI image of the soft tissue. Of course, fiducial marks or registration marks are required to align the two views. Also, one such view may have to be enlarged or reduced with respect to the other, which is readily done by adjusting the distance the video camera is from the image on the view box. The foreground object is then superimposed over the combined background.

While particular embodiments of the invention have been shown and described, it will be understood that the invention is not limited thereto. Many modifications may be made and will become apparent to those skilled in the art.

What is claimed is:

1. A method of creating a manipulable three-dimensional image of an object with respect to a background object, which comprises:
    digitizing a first planar view of a foreground object for memory storage,
    digitizing a second planar view of said foreground object for memory storage,
    digitizing first planar view of a background object for memory storage,
    digitizing a second planar view of said background object for memory storage,
    creating a three-dimensional data image of said foreground and said background objects from the digitized and stored first and second planar views of said objects,
    inputting scaling geometrical factors of the three-dimensional data images of said objects and adjusting the data images to scale the data images to each other, and
    displaying the data image of said background object and superimposing the data image of said foreground object on the data image of said background object.

2. The method in accordance with claim 1, wherein said first planar view is orthogonal with said second planar view.

3. The method in accordance with claim 1, wherein said background objective is a part of the human anatomy and said foreground object is an implant device.

4. The method in accordance with claim 3, wherein the part of the human anatomy is an image of the vaginal area and the implant device is a vaginal brachytherapy implant applicator suitable for receiving a plurality of radiation sources therein.

5. The method in accordance with claim 4, and including
    assigning radiation values for each of said radiation sources and predetermining therefor the resulting radiation at incremental locations on said vaginal area,
whereby said implant applicator is manipulated and said values for each of said radiation sources are reassigned until the optimal dose treatment is determined.

6. The method in accordance with claim 1, wherein said background object is an image of the breast area of the human anatomy and said foreground object includes a breast compression device and biopsy needle.

7. The method in accordance with claim 1, wherein said background object includes at least two different fiducial representations.

8. The method in accordance with claim 7, wherein said two different representations are an X-ray representation and a magnetic resonance imaging representation.

9. The method in accordance with claim 1, wherein the data images are scaled to each other before being displayed.

10. The method in accordance with claim 1, and including manipulating the data image of said foreground object with respect to the data image of said background object by either rotating or translating, or by rotating and translating, the data image of said foreground object.

11. The method in accordance with claim 1, wherein said foreground object includes a radiation source and is implantable in the body of a patient and said background object is a patient.

12. The method in accordance with claim 11, and including calculating isodose curves for determining the distribution of the radiation dosage delivered by the implanted radiation source.

13. A method of determining the distribution of radiation dosage delivered by a radiation source implanted in the body of a patient comprising the steps of digitizing a first planar view of an image of a treatment field of a patient receiving radiation treatment and having an applicator including a radiation source implanted therein, digitizing a second planar view of the treatment field including the applicator, digitizing a first planar view of the applicator, digitizing a second planar view of the applicator, generating a three-dimensional coordinate system for a data image of the applicator, creating the three-dimensional data image of the applicator and a three-dimensional data image of the treatment field from the digitized first and second planar views of the applicator and the treatment field, displaying the three-dimensional data images of the applicator and the treatment field, the data image of the treatment field being displayed in the background and the data image of the applicator being displayed in the foreground, manipulating the data image of the applicator to scale the data image of the applicator for aligning the data image of the applicator onto the data image of the applicator implanted in the treatment field, thereby superimposing the coordinate system on the treatment field, and specifying a plurality of locations in the coordinate system and calculating the radiation dosage at each location from a radiation source having a selected size in the applicator.

14. The method in accordance with claim 13, and including calculating isodose curves for determining the distribution of the radiation dosage delivered in the treatment field by the implanted applicator.

15. The method in accordance with claim 13, wherein the first and second planar views of the applicator and the first and second planar views of the treatment field are orthogonal.

16. The method in accordance with claim 13, wherein the first and second images of the treatment field are X-ray films.

17. The method in accordance with claim 13, wherein the data image of the applicator is manipulated to be aligned with the data image of the applicator implanted in the treatment field in two orthogonal views.

18. The method in accordance with claim 13, wherein the step of manipulating the three-dimensional data images is accomplished by calculation using the geometrical scaling factors pertaining to the applicator.

19. The method in accordance with claim 13, and including superimposing a computer generated image of a device used in radiation therapy other than the applicator on the image of the treatment field and computing the radiation dosages resulting from the use of the device.

20. The method in accordance with claim 13, wherein the first and second images of the treatment field are magnetic resonance images of the treatment field.

21. The method in accordance with claim 13, and including inputting data regarding the size of the radiation source and individual source positions in the applicator before calculating the radiation dosage of each location.

* * * * *